United States Patent [19]
Morgan et al.

[11] Patent Number: 6,037,166
[45] Date of Patent: Mar. 14, 2000

[54] ENZYMATIC KINETIC RESOLUTION OF AN INTERMEDIATE USEFUL FOR PREPARING SUBSTITUTED TRICYCLICS

[75] Inventors: William Brian Morgan, Chatham; Jinchu Liu, Edison, both of N.J.

[73] Assignee: Schering Corporation, Kenilworth, N.J.

[21] Appl. No.: 09/094,681

[22] Filed: Jun. 15, 1998

Related U.S. Application Data

[60] Provisional application No. 60/049,875, Jun. 17, 1997.

[51] Int. Cl.[7] .............................. C12P 17/12; C07C 1/04
[52] U.S. Cl. ........................................ 435/280; 435/122
[58] Field of Search ...................... 435/280, 122

[56] References Cited

FOREIGN PATENT DOCUMENTS

WO 95/10516  4/1995  WIPO .

OTHER PUBLICATIONS

J. Org. Chem. 1990, 55, 3341–3350.
Topics in Stereochemistry, N.L. Allinger, vol. 14, pp. 1–5.
Concise Encyclopedia Chemistry, (Walter de Gruyter, New York, 1994), pp. 106–107.
Chen et al, *Biorg. Med. Chem. Lett.*, 4 (1994), pp. 443–448.
Fortier et al, *Biotechnol. Lett.*, 8 (1986), pp. 777–782.
Paradkar et al, *J. Amer. Chem. Soc.*, 116 (1994), pp. 5009–5010.
Nakajima et al, *Int. J. Pept. Protein Res.*, 28 (1986), pp.179–185.
Gutman et al, *Tet. Lett.*, 33,27 (1992) pp. 3943–3946.
Asensio et al, *Tet. Lett.*, 32, 33 (1991), pp. 4197–4198.
Herradon et al, *Synlett*, (1995), pp. 599–602.
Orsat, et al, *J. Amer. Chem. Soc.*, 118 (1996), pp. 712–713.

*Primary Examiner*—Sandra E. Saucier
*Attorney, Agent, or Firm*—Anita W. Magatti

[57] ABSTRACT

The invention relates to a process for preparing a substituted (6,11-dihydro-5H-benzo[5,6]cyclohepta[1,2-b]pyridin-11-yl)piperidine compound of the formula (+)-I

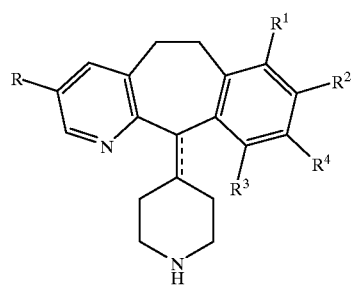

(+)-I wherein:
R, $R^1$, $R^2$, $R^3$ and $R^4$ are independently selected from the group consisting of hydrogen, halo, $C_1$–$C_6$ alkyl, amino, —$OCH_3$, —$OCF_3$ and $CF_3$, and the dotted line represents an optional double bond; comprising:
enzymatically catalyzing the acylation of a compound of the formula (±)-II

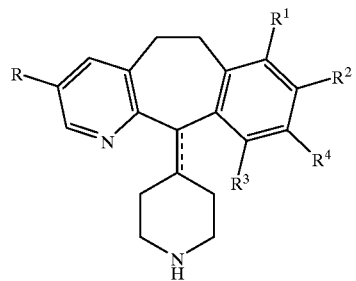

(±)-II wherein the variables are as defined above, and hydrolysing the product to obtain (+)-I.

9 Claims, No Drawings

ENZYMATIC KINETIC RESOLUTION OF AN INTERMEDIATE USEFUL FOR PREPARING SUBSTITUTED TRICYCLICS

This application claims benefit of Provisional Application 60/049875 Jun. 17, 1997.

BACKGROUND OF THE INVENTION

This invention provides an enzymatic process for preparing optically enriched intermediates useful in the preparation of substituted tricyclic compounds known as antihistamines and as inhibitors of farnesyl protein transferase (FPT). In particular, the process of this invention is useful in preparing intermediates useful in the preparation of FPT inhibitors disclosed, for example, in International Publication Number WO95/10516, published Apr. 20, 1995.

The use of enzymes for the synthesis of non-racemic chiral compounds is now well established. Since they are easy to use and readily available, hydrolases (proteases, esterases and lipases) have been used for the preparation of chirally pure molecules, under both aqueous and non-aqueous conditions. Enzyme catalyzed acylation reactions in non-aqueous solvents have been widely used for the kinetic resolution of racemic alcohols and amines. There are numerous examples in the literature of the selective acylation of a single enantiomer of a racemic primary amine:

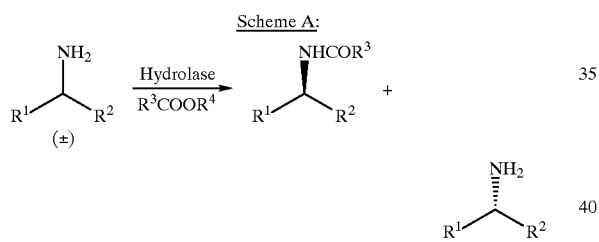

However, the enzymatic acylation of secondary and cyclic amines has been described less frequently:

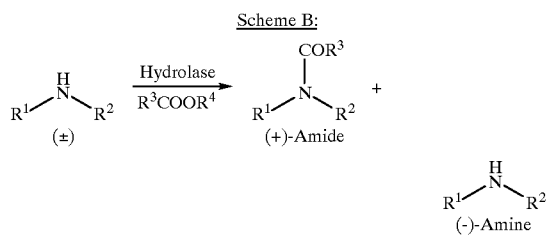

Most of the examples gleaned from the literature involve the acylation of chirally pure proline esters or amides catalyzed by alcalase (Chen et al, *Biorg. Med. Chem. Lett.*, 4 (1994), p. 443), clostridiopeptidase B (Fortier et al, *Biotechnol. Lett.*, 8 (1986), p. 777), α-chymotrypsin (Paradkar et al, *J. Amer. Chem. Soc.*, 116 (1994), p. 5009), and aminoacyl-t-RNA synthetase (Nakajima et al, *Int. J. Pept. Protein Res.*, 28 (1986), p. 1986). Examples illustrating the enzymatic acylation of chiral secondary amines are shown in the following reaction schemes:

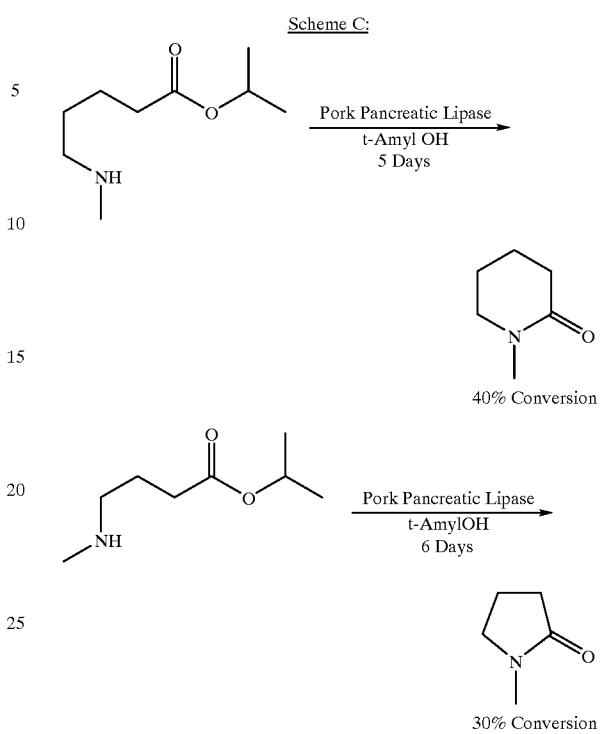

(Gutman et al, Tet. Lett., 33 (1992), p. 3943).

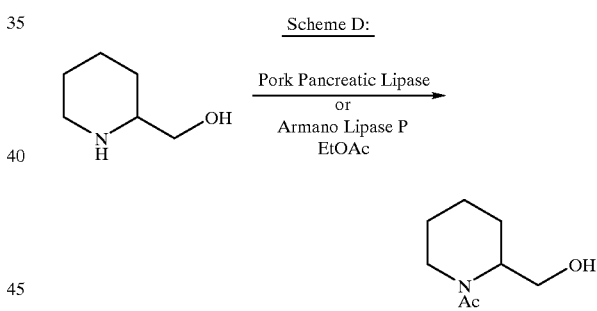

| PPL Catalyzed Acylation of 2-Hydroxymethylpiperidine | | | | |
|---|---|---|---|---|
| Enzyme Temp ° C./Time h | ees | eep | Conversion | E |
| PPL RT/4 | 0.23 | 0.70 | 0.25 | 7 |
| 40/4 | 0.13 | 0.59 | 0.18 | 4 |
| 0–5/30 | 0.39 | 0.51 | 0.43 | 4 |

(Asensio et al, Tet. Lett., 32 (1991), p. 4197).

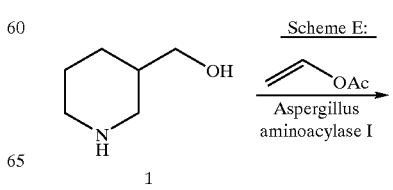

-continued

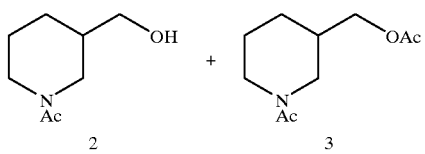

Enzymatic Acylation of 3-Hydroxymethylpiperidine

| Solvent | Enzyme mg/mmol | Vinyl Acetate equiv. | Time h | 2 (Yield) (ee) | 3 (Yield) (ee) |
|---|---|---|---|---|---|
| Vinyl Acetate | 300 | 50 | 91 | 29% (0.19) | 69% (n/d) |
| Acetonitrile | 300 | 5 | 94 | 37% (<0.02) | 42% (n/d) |
| CH$_2$Cl$_2$ | 100 | 2.5 | 7.5 | 68% (0) | — |

(Herradon et al, S. Synlett (1995), p. 599).

Scheme F:

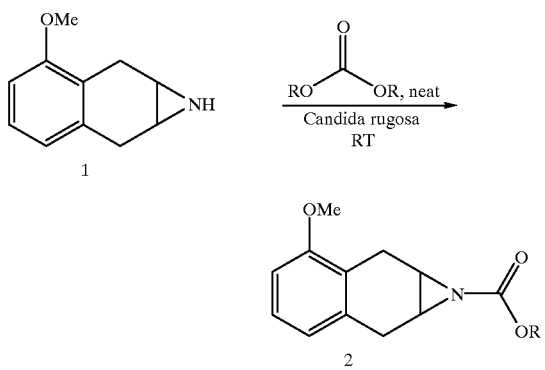

| Product | R | % yield | ee |
|---|---|---|---|
| 2a | methyl | 24 | 0.27 |
| 2b | ethyl | 31 | 0.31 |
| 2c | Allyl | 49 | 0.84 |

Conditions: Substrate, 1 mmol; Carbonate, 1 mL; Enzyme, 20 mg; RT, 45 h.
(Orsat, et al, J Amer. Chem. Soc., 118 (1996), p. 712).

Scheme G:

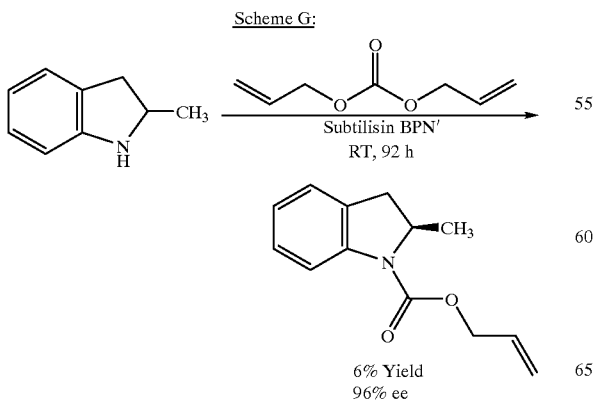

6% Yield
96% ee (Orsat, et al, J. Amer. Chem. Soc., 118 (1996), p. 712).

Generally, the resolutions suffer from low reactivity and/or selectivity. The reactions shown in schemes D and E probably occur by enzymatic acylation of the primary hydroxyl, followed by non-enzymatic intramolecular acyl transfer:

(In the above reaction Schemes A–H, the designation of the R substituents is for convenience in discussing those reactions, but does not correspond to the designation of the R substituents in the process claimed below.)

SUMMARY OF THE INVENTION

This invention provides a highly selective process for preparing a substituted (6,11-dihydro-5H-benzo[5,6]cyclohepta[1,2-b]-pyridin-11-yl) piperidine compound of the formula (+)-I

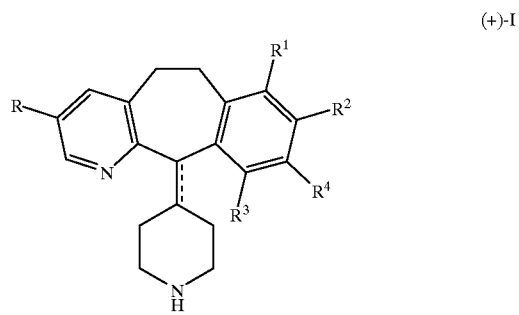

(+)-I wherein:

R, R$^1$, R$^2$, R$^3$ and R$^4$ are independently selected from the group consisting of hydrogen, halo, C$_1$–C$_6$ alkyl, amino, —OCH$_3$, —OCF$_3$ and CF$_3$, and the dotted line represents an optional double bond; comprising:

(1)

(a) enzymatically catalyzing the acylation of a compound of formula (±)-II, wherein the variables are as defined above, to obtain a compound of formula (+)-III

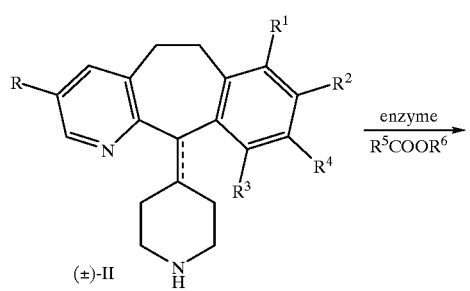

-continued

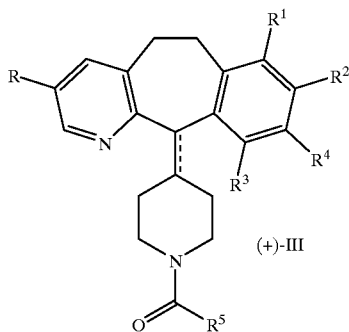

wherein the enzyme is a hydrolase and wherein the acylating agent is of the formula $R^5COOR^6$, wherein $R^5$ is $C_1$–$C_{15}$ alkyl, halo methyl, aryl, benzyl or benzyloxy, $R^6$ is $C_1$–$C_6$ alkyl, $C_1$–$C_6$ alkenyl, —$COR^7$, trifluoroethyl, —$CH_2CH(OCOR^7)CH_2OCOR^7$, halo methyl or benzyl, and $R^7$ is $C_1$–$C_{15}$ alkyl; and (b) hydrolysing the compound of formula (+)-III;
(c) optionally converting an undesired isomer from step (a) wherein a double bond is present to the racemate by heating, and resubjecting the racemate to enzymatic acylation and hydrolysis;

or (2) enzymatically catalyzing the acylation of a compound of formula (±)-IIa, wherein R, $R^1$, $R^2$, $R^3$ and $R^4$ are as defined above and the bond is a single bond, with a hydrolase, and wherein the acylating agent is as defined above.

Preferred compounds of formula (+)-I made by this process are those wherein $R^3$ is not hydrogen. Also preferred are compounds wherein R is halo. Still another group of preferred compounds is that wherein $R^1$ is hydrogen and R, $R^2$, and $R^3$ are selected form the group consisting of halo. Halo is preferably Cl or Br.

DETAILED DESCRIPTION

As used herein, the term "halo" means fluoro, chloro, bromo and iodo, with chloro and bromo being preferred.

As used herein, the term "aryl" means phenyl, naphthyl, substituted phenyl or substituted naphthyl, wherein "substituted" means 1–3 substituents independently selected form the group consisting of $C_1$–$C_6$ alkyl, $C_1$–$C_6$ alkoxy, halo, $NO_2$ and halo methyl.

Those skilled in the art recognize that suitable acylating enzymes may have opposing selectivity, and therefore may involve either direct or subtractive resolution. That is, some enzymes may acylate the desired isomer, requiring separation of the isomers, followed by hydrolysis to obtain the desired product (i.e., direct resolution, as claimed in step (1)), while others may acylate the undesired isomer, requiring only separation of the isomers (no hydrolysis) to obtain the desired isomer (i.e., subtractive resolution, as claimed in step (2)).

Commercially available enzymes suitable for use in the claimed process include Altus ChiroCLEC™ PC (*Pseudomonas cepacia*); Amano Lipase AY-30 (*Candida rugosa*); Meito Lipase MY (*Candida rugosa*), Meito Lipase AL (*Achromobacter* sp.), Meito Lipase QLC (*Alcaligenes* sp.) and Meito Lipase QLG (*Alcaligenes* sp.); Toyobo LIP-300 and LIP-301 (*Pseudomonas* sp.); Novo SP435 and Novozym 435 (*Candida antarctica* lipase B); Boehringer Mannheim Lipase (*Pseudomonas* sp.); and Boehringer Chirazyme™ L3 (*Candida rugosa*), Chirazyme™ L4 (*Pseudomonas* sp.) and Chirazyme™ L6 (*Pseudomonas* sp.).

Preferred enzymes are Toyobo LIP-300/301, Altus Chiro CLEC™ PC, Boehringer Mannheim Lipase, Novo SP435 and Novozym 435.

Acylating agents of formula $R^5COOR^6$ are commercially available or can be prepared by known methods. Preferred acylating agents are trifluoroethyl acetate (TFEOAc), trifluoroethyl butyrate (TFEOBu), trifluoroethyl isobutyrate (TFEOiBu), trifluoroethyl benzoate (TFEBenz), triacetin and tributyrin.

The enzymatic acylation may be carried out in a solvent such as an alkyl acetate such as methyl acetate (MeOAc) or isopropyl acetate, t-butyl methyl ether (TBME), tetrahydrofuran (THF), acetone, acetonitrile, t-amyl alcohol, t-butyl alcohol, pyridine or dioxane. Alternatively, the acylating agent may serve as the solvent. A preferred acylating agent which may also act as the solvent is trifluoroethyl isobutyrate.

The reaction is carried out in a temperature range of 0 to 50° C., preferably at 25 to 30° C. (e.g., ambient temperature). The reaction time ranges from 18 to 48 hours, with 24 hours being preferred. The enzyme is added at a ratio of about 1:2 times the amount of the starting material, preferably about 2 times the amount. The acylating agent is present at about 2 to 10 times the starting material, preferably about 3 times the amount of starting material when the enzyme is present at 2 times the amount of the starting material.

The hydrolysis is carried out using standard procedures well known in the art. For example, the acylated compound is refluxed with an acid such as $H_2SO_4$. The desired isomer is then recovered by precipitating out by adding a base such as NaOH.

The reaction is preferably carried out under anhydrous conditions. The solvent, or acylating agent when used as the solvent, can be anhydrous, or the solution of the starting material in the solvent, or acylating agent when used as the solvent, can be dried by azeotropic distillation before the enzyme is added. The enzyme should be dried under vacuum before adding to the solution, preferably to <700 ppm water.

The undesired (−) isomer can be recovered from enzymatic isobutyrylation of racemic II. Heating (−)-II in diphenyl ether or diethylene glycol dibutyl ether (5–15:1, v:v) at 200–260° C., preferably 210° C., for 0.5–26 hours results in complete racemization to racemic II which can be recovered in 77–95% yield with 93–99% purity. The recovered racemic II undergoes the enzymatic isobutyrylation under the same conditions as above.

Preferred embodiments of the claimed process are shown in the following reaction schemes:

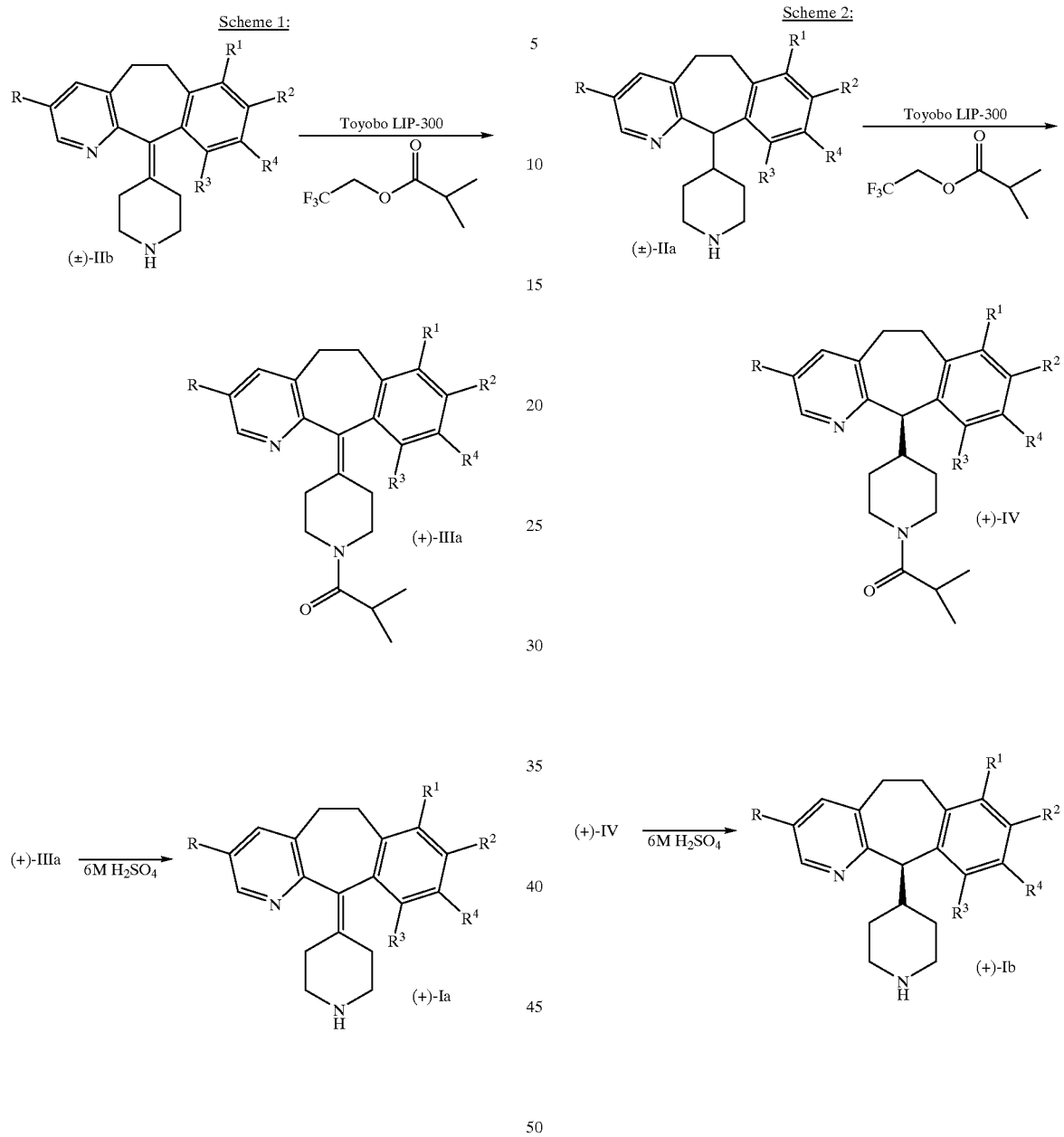

Scheme 3:
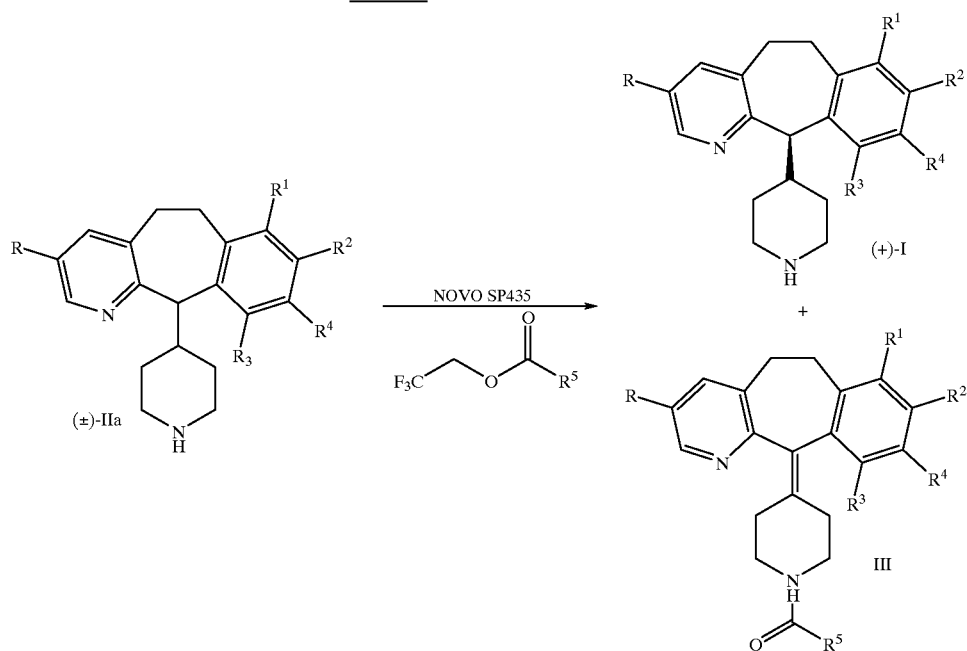
Especially preferred embodiments of the claimed process are represented by the following reaction schemes:
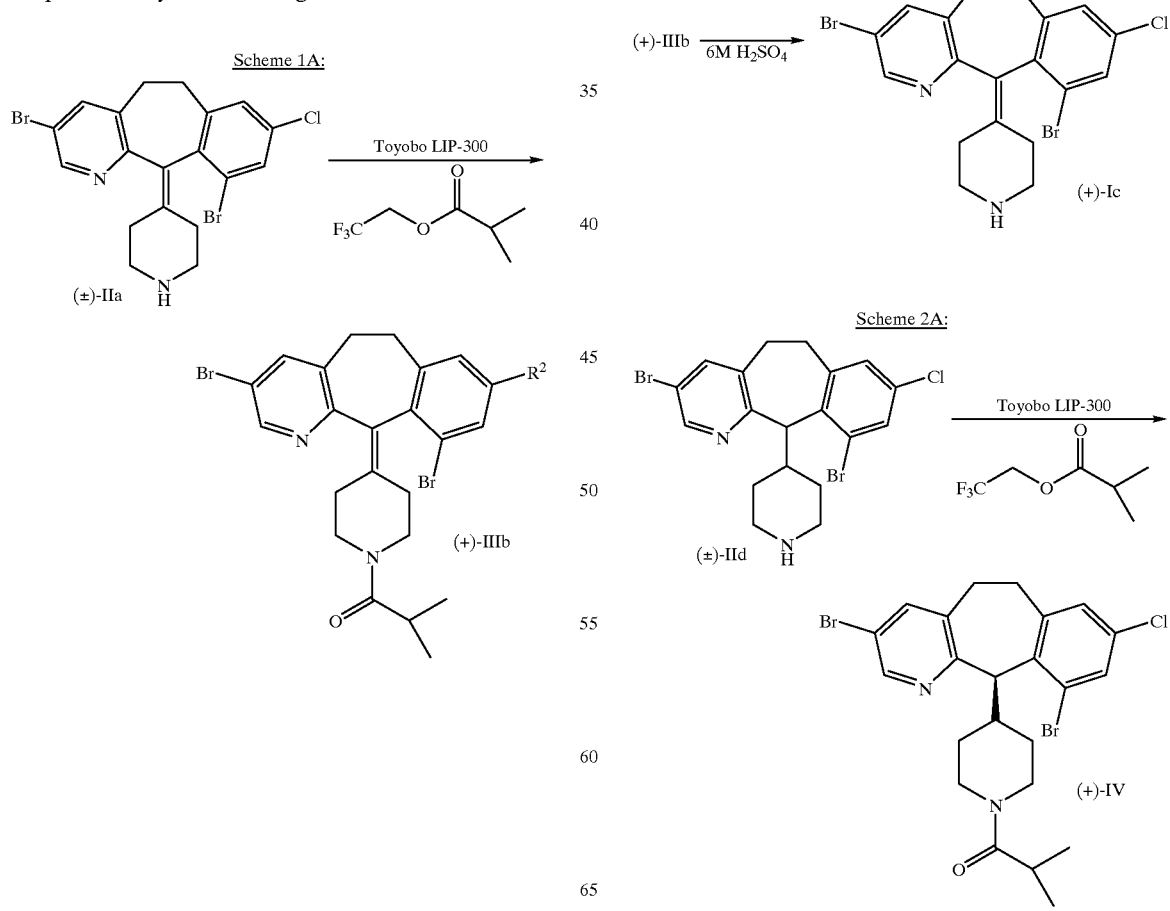

-continued

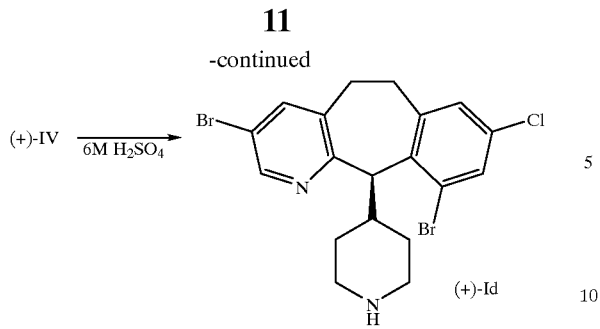

Previous methods used to resolve isomers to obtain compounds of formula I involved the resolution of a compound of formula (±)-IIa by chiral chromatography or chemical resolution using stiochiometric amounts of a resolving agent. The process claimed herein uses a biocatalyst to effect the resolution, the biocatalyst being reusable up to 15 times. Furthermore, compounds IIb are chiral atropisomers at room temperature due to restricted rotation about the double bond. However, the isomers can be racemized at high temperatures. By carrying out the enzymatic resolution of IIb, the undesired (−) isomer can be isolated, racemized at 200–260° C., preferably at 210° C., and then subjected to a further enzymatic acylation to increase throughput of (±)-IIIa.

The products of this process are intermediates useful in the preparation of tricyclic compounds useful as farnesyl protein transferase inhibitors such as those disclosed in International Publication Number WO95/10516, published Apr. 20, 1995.

The following tables show the results of varying the various parameters of the reactions. In most of the tables, the compound of formula I prepared by the process has the following substituents: R and $R^3$ are each bromo, $R^1$ and $R^4$ are each hydrogen and $R^2$ is chloro; those skilled in the art will recognize that compounds with different R-group substitution are expected to react in a similar manner. In the tables and elsewhere in this application, the terms have the following meanings: $ee_s$ is the enantiomeric excess of the unreacted starting material; $ee_p$ is the enantiomeric excess of the product; c is the conversion ($ee_s/(ee_s+ee_p)$); E is the Enantiomeric Ratio: ($\ln[(1-ee_s)(1-c)/\ln[(1+ee_s)(1-c)]$ or $\ln[1-c(1+ee_p)]/\ln[1-c(1+ee_p)]$); Ac is acetyl, OAc is acetate, Me is methyl, Et is ethyl, Pr is propyl and TFE is trifluoroethyl.

ENZYMATIC TRANSESTERIFICATION

A. Screen Results

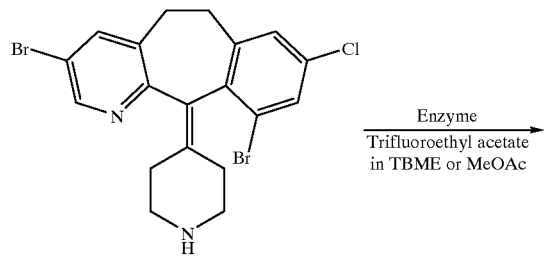

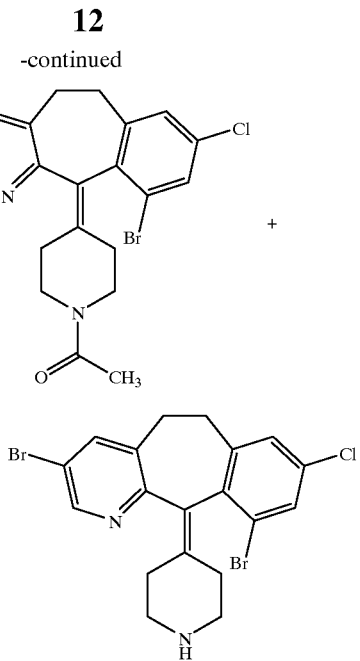

General Procedure: TFEOAc (0.06 mL, 20 equivs.) was added to a mixture of (±)-IIc (10 mg) and the enzyme (2–100 mg) in TBME (1.0 mL), except for Runs 1 and 4 which were run in the presence of $CaCO_3$ (30–40 mg) with MeOAc (1.0 mL) as both solvent and acylating agent. The reactions were shaken at 250 rpm at ambient temperature and monitored by thin layer chromatography. Reactions of interest were analyzed by chiral HPLC, the results of which are shown in Table 1.

TABLE 1

(±)-IIc Acetylation Screen: Results from 248 Enzyme Preparations

| Run | Enzyme | Wt mg | Time h | $ee_s$ | $ee_p$ | c | E |
|---|---|---|---|---|---|---|---|
| 1 | Altus ChiroCLEC PC | 4.1 | 45 | 0.22 | 0.60 | 0.26 | 5 |
| 2 | Amano Lipase AY | 16 | 40 | 0.18 | 0.19 | 0.48 | 2 |
| 3 | Meito Lipase MY | 18 | 40 | 0.18 | 0.17 | 0.51 | 2 |
| 4 | Toyobo LIP-300 | 7.0 | 45 | 0.22 | 0.66 | 0.25 | 6 |
| 5 | Toyobo LIP-300 | 18 | 16 | 0.93 | 0.58 | 0.61 | 12 |
| 6 | Boehringer Chirazyme L3 | 16 | 40 | 0.14 | 0.18 | 0.43 | 2 |
| 7 | Boehringer Chirazyme L4 | 12 | 40 | 0.11 | 0.20 | 0.35 | 2 |
| 8 | Boehringer Chirazyme L6 | 15 | 40 | 0.03 | 0.04 | 0.42 | 1 |
| 9 | Meito Lipase AL | 29.4 | 63.5 | 0.19 | 0.11 | 0.64 | 2 |
| 10 | Meito Lipase QLC | 53.6 | 63.5 | 0.55 | 0.24 | 0.69 | 3 |
| 11 | Meito Lipase QLG | 94.2 | 63.5 | 0.69 | 0.34 | 0.67 | 4 |
| 12 | Beohringer Pseudomonas sp. | 2 | 4 | 0.676 | 0.687 | 0.50 | 11 |

Conditions: Runs 2, 3, 5–11: (±)-IIc, 10 mg; Trifluoroethyl Acetate, 20 equiv; TBME, 1.0 mL; RT, 250 rpm. Runs 1, 4: (±)-IIc, 10 mg; $CaCO_3$, 30–40 mg; MeOAc, 1.0 mL (as solvent and acylating agent); RT; 250 rpm. Run 12: (±)-IIc, 12 mg; Trifluoroethyl acetate, 5 equiv.; TBME, 1.0 mL; RT, 250 rpm

B. The Effect of Solvent

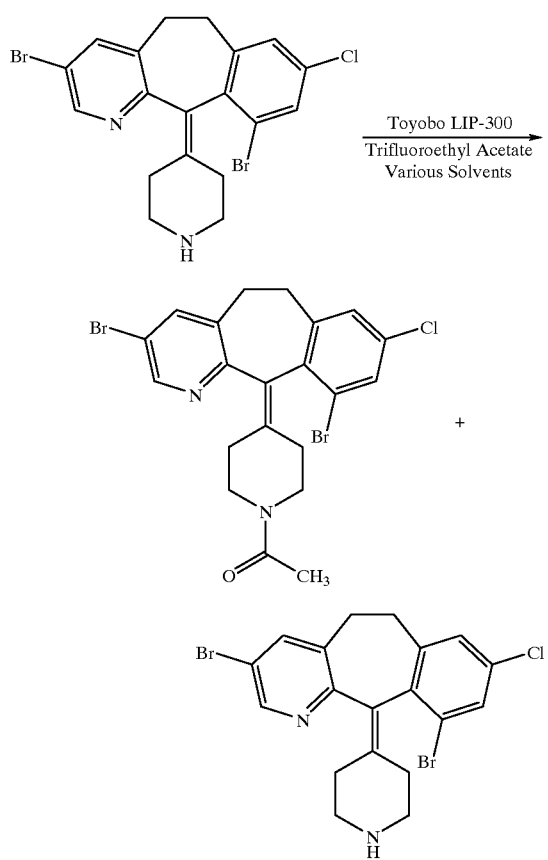

General Procedure: TFEOAc (0.2 mL, 40 equivs.) was added to a mixture of (±)-IIc (19–25 mg) and Toyobo LIP-300 (19–25 mg) in the appropriate solvent (2.0 mL). The reactions were shaken at 250 rpm at +4° C. and monitored by TLC and chiral HPLC. The results are in Table 2.

TABLE 2

The Effect of Solvent on the Acetylation of (±)-IIc Using Toyobo LIP-300

| Run | Solvent | Time h | $ee_s$ | $ee_p$ | c | E |
|---|---|---|---|---|---|---|
| 1 | MeOAc | 91 | 0.21 | 0.46 | 0.31 | 3 |
| 2 | nPrOAc | 91 | 0.04 | 0.03 | 0.60 | 1 |
| 3 | TBME | 91 | 0.65 | 0.64 | 0.50 | 9 |
| 4 | Toluene | 91 | 0.01 | n/d | n/d | n/d |
| 5 | THF | 91 | 0.39 | 0.51 | 0.43 | 4 |
| 6 | Acetone | 91 | 0.09 | 0.32 | 0.21 | 2 |
| 7 | MeCN | 26 | 0.24 | 0.77 | 0.24 | 10 |
|   |       | 91 | 0.32 | 0.66 | 0.32 | 7 |
| 8 | $CH_2Cl_2$ | 91 | 0.01 | n/d | n/d | n/d |
| 9 | tAmylOH | 91 | 0.03 | 0.37 | 0.07 | 2 |
| 10 | tBuOH | 91 | 0.04 | 0.35 | 0.10 | 2 |
| 11 | Pyridine | 91 | 0.02 | 0.06 | 0.23 | 1 |
| 12 | pDioxane | 91 | 0.13 | 0.33 | 0.28 | 2 |

Conditions: (±)-IIc, 19–25 mg; Toyobo LIP-300, 19–25 mg; Trifluoroethyl Acetate, 40 equivs; Solvent, 2.0 mL; 250 rpm; +4° C.

C. The Effect of Acylating Agent

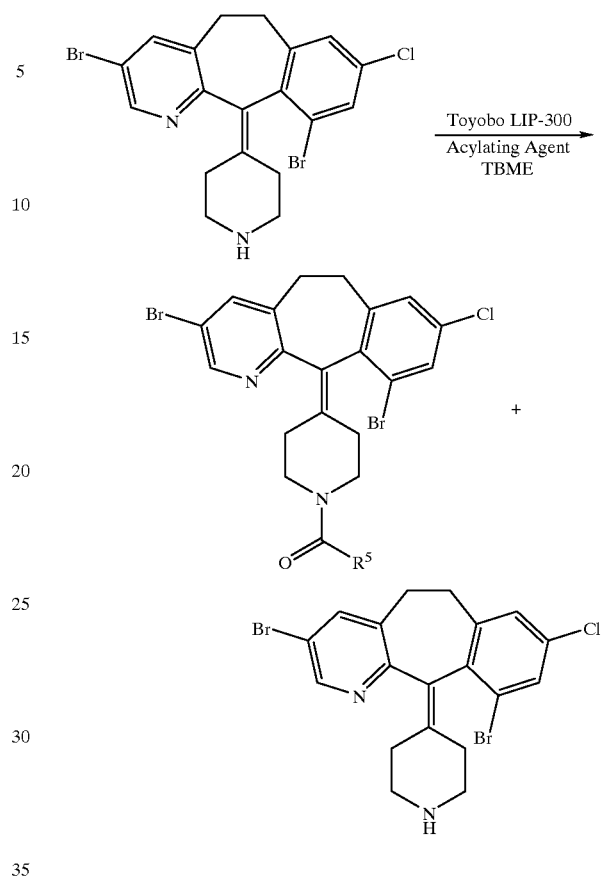

General Procedure: The acylating agent (20 equivs.) was added to a mixture of (±)-IIc (20 mg) and enzyme (19–26 mg) in TBME (2.0 mL), except for Run 8 which used MeOAc (2.0 mL) as solvent and acylating agent, Run 11 which used 10 equivalents of acylating agent and Run 18 which used 88 equivalents of acylating agent. The reactions were shaken at 250 rpm at ambient temperature, except Run 11 which was shaken at +4° C., and the reactions monitored by TLC and chiral HPLC. With the exception of Runs 4, 5, 10, 11, 17, 18 and 19 all reactions were subjected to workup in which the product and the starting material were separated by preparative TLC and the enantiomeric excesses determined separately. The results are collected in Table 3.

TABLE 3

The Effect of Acylating Agent on the Acylation of (±)-IIc Using Toyobo LIP-300

| Run | Acylating Agent | Time h | $ee_s$ | $ee_p$ | c | E |
|---|---|---|---|---|---|---|
| 1 | Trifluoroethyl Acetate | 23.75 | 0.92 | 0.82 | 0.53 | 32 |
|   |   | Isolated | 0.91 | 0.84 | 0.52 | 35 |
| 2 | Trifluoroethyl Acetate | 15 | 0.92 | 0.79 | 0.54 | 28 |
|   |   | 16.5 | 0.95 | 0.80 | 0.54 | 33 |
|   |   | Isolated |   |   |   |   |
| 3 | Trifluoroethyl Acetate | 15 | 0.91 | 0.82 | 0.53 | 31 |
|   |   | 16.5 | 0.93 | 0.85 | 0.52 | 43 |
|   |   | Isolated |   |   |   |   |
| 4 | Trifluoroethyl Chloroacetate | 27.00 | 0.05 | 0.47 | 0.09 | 3 |
| 5 | Trifluoroethyl Dichloroacetate | 27.00 | 0.01 | 0.08 | 0.08 | 1 |

TABLE 3-continued

The Effect of Acylating Agent on the Acylation of (±)-IIc Using Toyobo LIP-300

| Run | Acylating Agent | Time h | ee$_s$ | ee$_p$ | c | E |
|---|---|---|---|---|---|---|
| 6 | Trifluoroethyl Butyrate | 27.00 | 0.87 | 0.90 | 0.49 | 53 |
|   |   | Isolated | 0.95 | 0.77 | 0.55 | 28 |
| 7 | Trifluoroethyl Butyrate | 15 | 0.68 | 0.88 | 0.44 | 33 |
|   |   | 17 Isolated | 0.77 | 0.87 | 0.47 | 34 |
| 8 | Trifluoroethyl Hexanoate | 27.00 | 0.88 | 0.80 | 0.52 | 26 |
|   |   | Isolated | 0.94 | 0.66 | 0.59 | 17 |
| 9 | Trifluoroethyl Laurate | 27.00 | 0.39 | 0.83 | 0.32 | 16 |
|   |   | Isolated | 0.70 | 0.78 | 0.47 | 17 |
| 10 | Methyl Acetate (neat) | 23.75 | 0.07 | 0.42 | 0.14 | 3 |
| 11 | Isopropenyl Acetate | 7 | 0.12 | 0.28 | 0.31 | 2 |
| 12 | Triacetin | 23.75 | 0.37 | 0.89 | 0.30 | 24 |
|   |   | Isolated | 0.53 | 0.93 | 0.36 | 48 |
| 13 | Triacetin | 23.75 | 0.37 | 0.89 | 0.30 | 14 |
|   |   | 20.75 Isolated | 0.38 | 0.96 | 0.28 | 81 |
| 14 | Tributyrin | 27.00 | 0.29 | 0.79 | 0.27 | 11 |
|   |   | Isolated | 0.55 | 0.94 | 0.37 | 60 |
| 15 | Tributyrin | 15 | 0.30 | 0.81 | 0.27 | 13 |
|   |   | 20.75 Isolated | 0.45 | 0.84 | 0.35 | 18 |
| 16 | Trifluoroethyl Benzyl Carbonate | 15 | 0.86 | 0.71 | 0.55 | 16 |
|   |   | 20.75 Isolated | 0.90 | 0.61 | 0.59 | 12 |
| 17 | Dibenzyl carbonate | 15 | 0.06 | n/d | n/d | n/d |
| 18 | Ethyl Butyrate | 15 | 0.02 | 0.59 | 0.04 | 4 |
| 19 | Trifluoroethyl benzoate | 26 | 0.235 | 0.990 | 0.192 | 250 |

Conditions: (±)-IIc, 20 mg; Toyobo LIP-300, 19–26 mg; TBME, 2 mL; Acylating agent, 20 equivs.; 250 rpm; RT. Exceptions: Run 10, MeOAc as solvent and acylating agent; Run 11, Acylating agent 10 equivs. and +4° C.; Run 18, 88 equivs. of acylating agent; Run 19, (±)-IIc, 10 mg; Acylating agent, 5 equivs.

ENZYMATIC ISOBUTYRYLATION OF (±)-IIc

A. Enzyme Survey

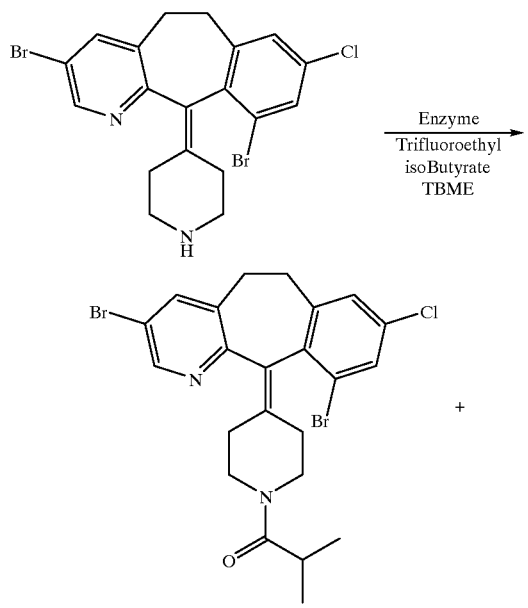

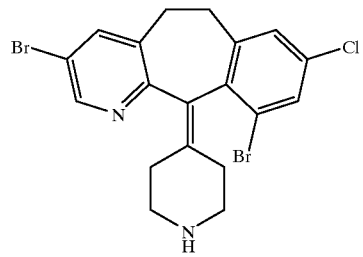

General Procedure: A mixture of (±)-IIc (25 mg), TFEOiBu (0.04 mL, 5 equivs.), 4 Å molecular sieves (25–40 mg) and enzyme (6–27 mg) in TBME (1.0 mL) was shaken at ambient temperature and 250 rpm for 23.5 h. The reactions were monitored by chiral HPLC and the results are collected in Table 4.

TABLE 4

Isobutyrylation of (±)-IIc with Various Enzyme Preparations in TBME

| Run | Source | Enzyme | ee$_s$ | ee$_p$ | c | E |
|---|---|---|---|---|---|---|
| 1 | Sawa | Immob. Lipase LIP-301 lot #33580 | 0.610 | 0.982 | 0.383 | 203 |
| 2 | Sawa | Lipoprotein Lipase LPL-701 lot #0514A | 0.245 | 0.982 | 0.200 | 143 |
| 3 | Toyobo | Lipase (LIP-300) | 0.712 | 0.985 | 0.419 | 278 |
| 4 | Toyobo | Lipoprotein Lipase (LPL-311) Type A | 0.059 | 0.920 | 0.060 | 25 |
| 5 | Toyobo | Lipoprotein lipase (LPL-701) | 0.267 | 0.979 | 0.214 | 123 |
| 6 | Toyobo | Lipoprotein lipase (Type A) | 0.079 | 0.932 | 0.078 | 31 |
| 7 | Boehringer | chirazyme L4 | 0.092 | 0.910 | 0.092 | 23 |
| 8 | Boehringer | chirazyme L6 | 0.260 | 0.977 | 0.210 | 110 |
| 9 | Altus | ChiroClec PC | 0.053 | 0.908 | 0.055 | 22 |
| 10 | Toyobo | LIP-300 lot #36510 | 0.724 | 0.987 | 0.423 | 335 |
| 11 | Toyobo | LPL-311 lot #53250 | 0.037 | 0.922 | 0.038 | 26 |

Conditions: (±)-IIc (25 mg, 50 mM), Trifluoroethyl isobutyrate (5 eq), Enzyme (6–27 mg), 4Å Sieves (25–40 mg), TBME (1.0 mL), 250 rpm, RT, 23.5 h.

B. Effect of Solvent

General Procedure: For Runs 1–9, (±)-IIc (49–57 mg), 4 Å molecular sieves (47–59 mg) and Toyobo LIP-300 (50–55 mg) were suspended in the appropriate solvent (2.0 mL) and trifluoroethyl isobutyrate (0.08 mL, 5 equivs.) added, except for Runs 1–3 where the solvent was used as the acylating agent. The reactions were shaken at 250 rpm at ambient temperature for 22.5 h.

For Runs 10–25, mixtures of (±)-IIc (70 mg), Toyobo LIP-300 (70 mg) and trifluoroethyl isobutyrate (5 equivs.), except Runs 17–23 which used solvent as acylating agent, in the appropriate solvent (2.0 mL) were shaken at 300 rpm and 30° C. for 24 h.

The results of the chiral HPLC analysis are collected in Table 5.

TABLE 5

Effect of Solvent on the isoButyrylation of (±)-IIc Using Toyobo LIP-300

| Run | Solvent | Acylating Agent | $ee_s$ | $ee_p$ | c | E |
|---|---|---|---|---|---|---|
| 1 | Trifluoroethyl isobutyrate | None | 0.445 | 0.947 | 0.320 | 57 |
| 2 | Ethyl isobutyrate | None | 0.106 | 0.881 | 0.107 | 18 |
| 3 | Methyl isobutyrate | None | 0.032 | n/d | n/d | n/d |
| 4 | TBME | TFEOiBu | 0.535 | 0.984 | 0.352 | 217 |
| 5 | Toluene | TFEOiBu | 0.145 | 0.917 | 0.137 | 27 |
| 6 | THF | TFEOiBu | 0.147 | 0.926 | 0.137 | 30 |
| 7 | Acetone | TFEOiBu | 0.097 | 0.990 | 0.089 | 219 |
| 8 | MeCN | TFEOiBu | 0.134 | 0.924 | 0.126 | 29 |
| 9 | pDioxane | TFEOiBu | 0.086 | >0.99 | 0.080 | 217 |
| 10 | TBME | TFEOiBu | 0.618 | 0.973 | 0.388 | 137 |
| 11 | 10% Et$_3$N/TBME | TFEOiBu | 0.851–0.917 | 0.936–0.938 | 0.476–0.494 | 83–102 |
| 12 | 10% Toluene/TBME | TFEOiBu | 0.541 | 0.968 | 0.359 | 106 |
| 13 | 20% Toluene/TBME | TFEOiBu | 0.447 | 0.967 | 0.316 | 93 |
| 14 | 30% Toluene/TBME | TFEOiBu | 0.388 | 0.965 | 0.287 | 82 |
| 15 | 40% Toluene/TBME | TFEOiBu | 0.316 | 0.964 | 0.247 | 75 |
| 16 | 50% Toluene/TBME | TFEOiBu | 0.241 | 0.966 | 0.200 | 72 |
| 17 | Methyl isobutyrate neat | None | 0.022 | n/d | n/d | n/d |
| 18 | 10% EtOiBu/TBME | None | 0.134 | 0.988 | 0.119 | 192 |
| 19 | 10% EtOiBu/TBME | None | 0.029 | 0.956 | 0.030 | 46 |
| 20 | 20% EtOiBu/TBME | None | 0.059 | 0.991 | 0.056 | 226 |
| 21 | 30% EtOiBu/TBME | None | 0.07 | 0.991 | 0.066 | 242 |
| 22 | 40% EtOiBu/TBME | None | 0.076 | 0.991 | 0.071 | 251 |
| 23 | 50% EtOiBu/TBME | None | 0.092 | 0.991 | 0.085 | 251 |
| 24 | TBME/Dried Enzyme | TFEOiBu | 0.856–0.943 | 0.944–0.946 | 0.476–0.499 | 96–130 |
| 25 | 20% Et$_3$N/TBME | TFEOiBu | 0.875–0.960 | 0.872–0.877 | 0.501–0.523 | 42–60 |

Conditions: Runs 1–9: (±)-IIc (50 mg, 50 mM), Toyobo LIP-300 (50–55 mg), TFEOiBu (5 eq., except Runs 1–3 which used solvent as acylating agent), Solvent (2.0 mL), 4Å Sieves (47–59 mg), 250 rpm, RT, 22.25 h.
Runs 10–25 (±)-IIc (70 mg, 75 mM), Toyobo LIP-300 (70 mg); Solvent (2.0 mL), TFEOiBu (5 equiv., except Runs 17–23 which used solvent as acylating agent), 30° C., 300 rpm, 24 h.

ENZYMATIC RESOLUTION OF (±)-IId

A. Acylation of (±)-IId Using ChiroCLEC PC

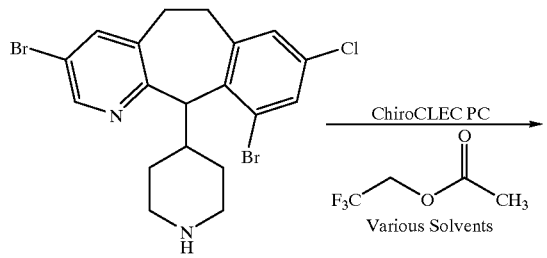

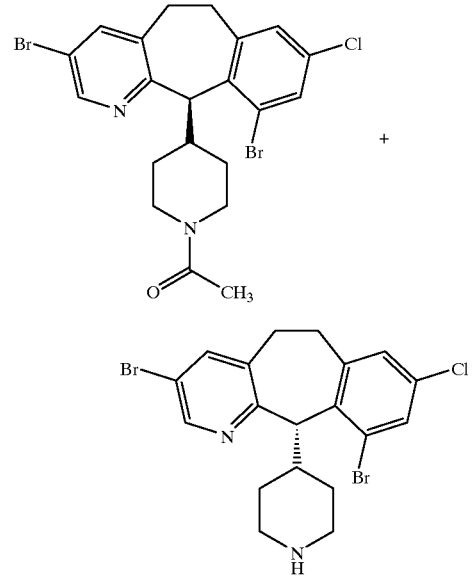

TABLE 6

Acetylation of (±)-IId using ChiroCLEC PC in Various Solvents

| Run | Solvent | Time h | $ee_s$ | $ee_p$ | Conversion | E |
|---|---|---|---|---|---|---|
| 1 | EtOAc | 20.25 | 0.02 | 0 | n/d | n/d |
| 2 | PrOAc | 20.25 | 0.00 | 0 | n/d | n/d |
| 3 | TBME | 20.25 | 0.08 | 0.67 | 0.11 | 6 |
| 4 | Acetone | 20.25 | 0.07 | 0.48 | 0.12 | 3 |
| 5 | MeCN | 3.75 | 0.56 | 0.83 | 0.40 | 18 |
| 6 | tAmyl Alcohol | 20.25 | 0.02 | 0.45 | 0.05 | 3 |
| 7 | Pyridine | 20.25 | 0.01 | 0.20 | 0.03 | 2 |
| 8 | 3-Me-3-pentanol | 20.25 | 0.09 | 1.00 | 0.08 | n/d |

Conditions: (±)-IId (5–9 mg), TFEOAc (12–20 equiv.), CLEC PC (4.5–9.1 mg), Solvent (1.0 mL), RT, 250 rpm.

B. Acylation of (±)-IId Using Toyobo LIP-300

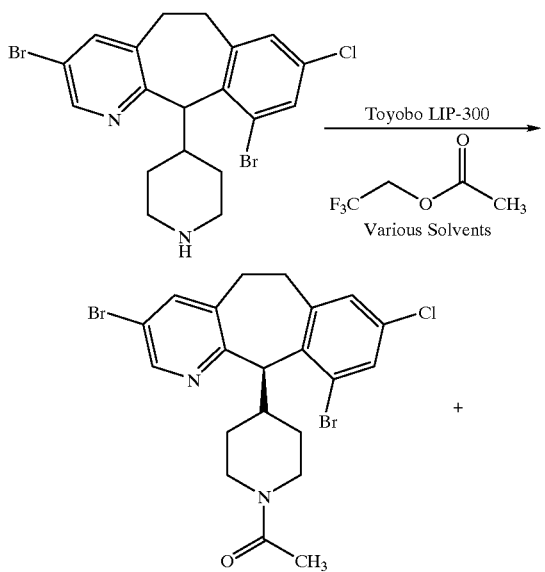

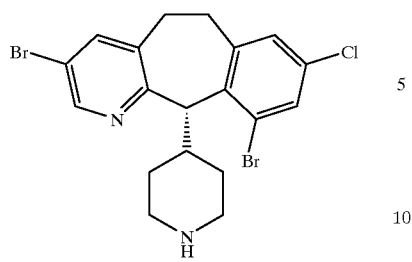
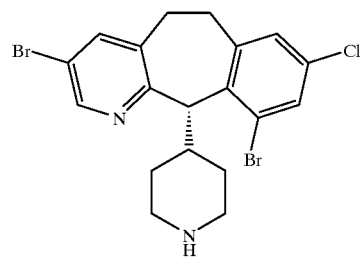

TABLE 7

Acetylation of (±)-IId using Toyobo LIP-300 in Various Solvents

| Run | Solvent | Time h | ee$_s$ | ee$_p$ | Conversion | E |
|---|---|---|---|---|---|---|
| 1 | MeOAc | 29.75 | 0.27 | >0.95 | 0.21 | >100 |
| 2 | PrOAc | 29.75 | 0.02 | n/d | n/d | n/d |
| 3 | TBME | 29.75 | 0.39 | 0.69 | 0.36 | 8 |
| 4 | Toluene | 29.75 | 0.01 | 0.27 | 0.04 | 2 |
| 5 | THF | 29.75 | 0.00 | n/d | n/d | n/d |
| 6 | Acetone | 29.75 | 0.21 | 0.51 | 0.29 | 4 |
| 7 | MeCN | 2.25 | 0.15 | 0.82 | 0.15 | 12 |
|   |   | 4.75 | 0.31 | 0.91 | 0.26 | 30 |
|   |   | 21.75 | 0.82 | 0.85 | 0.49 | 31 |
|   |   | 29.75 | 0.89 | 0.80 | 0.53 | 26 |
| 8 | Dichloromethane | 29.75 | 0.02 | n/d | n/d | n/d |
| 9 | tAmyl Alcohol | 29.75 | 0.04 | 0.38 | 0.11 | 2 |
| 10 | Pyridine | 29.75 | 0.02 | n/d | n/d | n/d |
| 11 | Dioxane | 29.75 | 0.12 | n/d | n/d | n/d |
| 12 | MeOAc, neat | 27.25 | 0.47 | 0.92 | 0.34 | 41 |
| 13 | Trifluoroethyl Acetate, neat | 27.25 | 0.17 | 0.49 | 0.25 | 3 |
| 14 | isoPropenyl Acetate, neat | 3 | Complete reaction | | | |

Conditions: (±)-IId, 6.5–12.8 mg; TFEOAC, 0.08 mL, 30–50 equiv.; Enzyme, 2.8–8.4 mg; Solvent, 2.0 mL; RT, 250 rpm., except Runs 12–14 which used solvent (2.0 mL) as acylating agent C. Isobutyrylation of (±)-IId Using Toyobo LIP-300

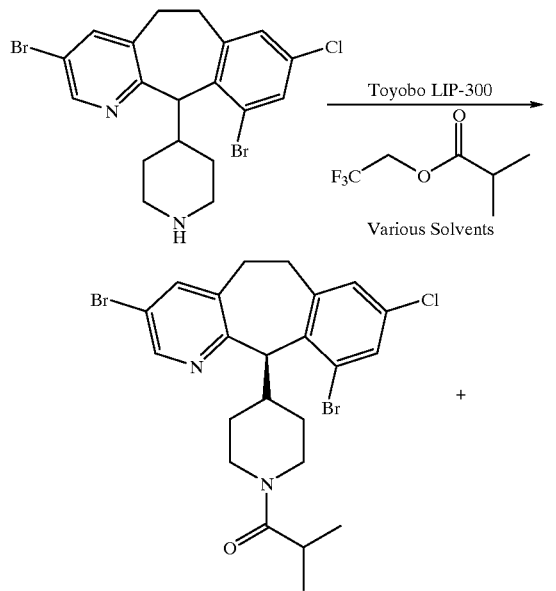

TABLE 8

Isobutyrylation of (±)-IId Using Toyobo LIP-300 in Various Solvents

| Run | Solvent | ees | eep | Converison | E |
|---|---|---|---|---|---|
| 1 | TBME | 0.818 | 0.971 | 0.457 | 174 |
| 2 | THF | 0.474 | 0.889 | 0.348 | 27 |
| 3 | Toluene | 0.202 | 0.962 | 0.173 | 63 |
| 4 | MeCN | 0.236 | 0.932 | 0.202 | 36 |

Conditions: (±)-IId, 50 mg; Toyobo LIP-300, 50 mg; TFEOiBu, 0.08 mL, 5 equivs.; Solvent, 2.0 mL; 250 rpm; RT.

D. Acylation of (±)-IId Using NOVO SP435

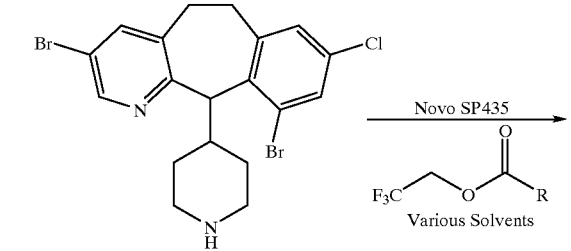

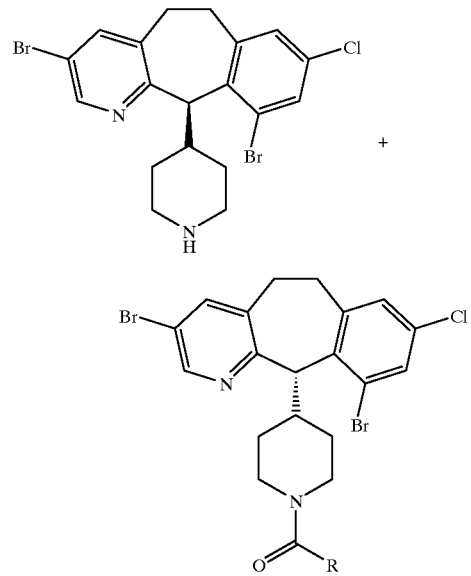

TABLE 9

Acetylation of (±)-IId using Novo SP435 in Various Solvents/Temperatures

| Run | Reaction | Time h | ee$_s$ | ee$_p$ | Conversion | E |
|---|---|---|---|---|---|---|
| 1 | MeOAc | 15.50 | 0.45 | 0.18 | 0.72 | 2 |
| 2 | MeOAc | 1.00 | 0.68 | 0.70 | 0.49 | 11 |
| 3 | PrOAc | 15.5 | 0.17 | 0.61 | 0.22 | 5 |
| 4 | TBME | 40 | 0.09 | >0.95 | 0.09 | 43 |
| 5 | Toluene | 40 | 0.05 | 0.85 | 0.06 | 13 |
| 6 | THF | 15.5 | 0.82 | 0.31 | 0.72 | 4 |
| 7 | Acetone | 15.5 | 0.33 | 0.78 | 0.30 | 11 |
| 8 | Acetone | 1 | 0.72 | 0.64 | 0.53 | 10 |
| 9 | MeCN | 15.5 | 0.24 | 0.02 | 0.91 | 1 |
| 10 | MeCN | 1 | >0.95 | 0.43 | 0.69 | 8 |
| 11 | MeCN, 0° C. | 1.25 | 0.55 | 0.73 | 0.43 | 11 |
| 12 | MeCN/NaHCO$_3$; −2 to −5° C. | 1.5 | 0.39 | 0.77 | 0.34 | 11 |
| 13 | Dichloromethane | 40 | 0.07 | >0.95 | 0.07 | 42 |
| 14 | tAmylOH | 15.5 | 0.02 | >0.95 | 0.02 | 40 |
| 15 | Pyridine | 15.5 | 0.52 | 0.35 | 0.60 | 3 |

Conditions: Runs 1, 3–7, 9, 13–15: (±)-IId, 7–11 mg; TFEOAc, 50 mL, 14–25 equiv.; SP435, 8–13 mg; Solvent, 2.0 mL, RT, 250 rpm.
Runs 2, 8, 10–12: (±)-IId, 12–15 mg; TFEOAc, 100 mL, 25–31 equiv. (except Run 2 which used solvent as the acylating agent); SP 435, 4–7 mg; Solvent, 2.0 mL; 250 rpm.

TABLE 10

Acylation of (±)-IId with Various Acylating Agents catalyzed by Novo SP435

| Run | Solvent/ Acylating Agent | Acylating Agent equiv. | Time h | ee$_s$ | ee$_p$ | c | E |
|---|---|---|---|---|---|---|---|
| 1 | MeOAc | Neat | 66.25 | >0.95 | 0.09 | 0.91 | n/d |
| 2 | MeOAc | Neat | 2.0 | 0.26 | 0.83 | 0.24 | 13 |
| 3 | MeOAc | Neat | 1.0 | 0.68 | 0.70 | 0.49 | 11 |
| 4 | EtOAc | Neat | 66.25 | >0.95 | 0.11 | 0.90 | n/d |
| 5 | PrOAc | Neat | 66.25 | 0.74 | 0.47 | 0.61 | 6 |
| 6 | iPropenylOAc (neat) | Neat | 66.25 | 0 | 0 | 1.00 | n/d |
| 7 | iPropenylOAc | 12 | 66.25 | 0 | 0 | 1.00 | n/d |
| 8 | Acetic Anhydride | 10 | 66.25 | 0 | 0 | 1.00 | n/d |
| 9 | TFEOAc | 14 | 662.5 | 0.60 | 0.29 | 0.67 | 3 |
| 10 | TFEOAc/Acetone −5° C. | 11 | 20.75 | 0.16 | 0.76 | 0.18 | 8 |
| 11 | EtOAcCl | Neat | 66.25 | 0 | 0 | 0 | n/d |
| 12 | TFEOAcCl | 17 | 66.25 | 0 | 0 | 0 | n/d |
| 13 | Propionic Anhydride | 14 | 66.25 | 0 | 0 | 1.00 | n/d |
| 14 | Butyric Anhydride | 17 | 66.25 | 0 | 0 | 1.00 | n/d |
| 15 | isoButyric Anhydride | 17 | 66.25 | 0 | 0 | 1.00 | n/d |
| 16 | EtOBu | Neat | 66.25 | 0 | 0 | 1.00 | n/d |
| 17 | TFEOBu | 17 | 66.25 | 0.07 | 0.85 | 0.07 | 14 |
| 18 | TFEOBu/MeCN | 12 | 20.75 | 0.08 | n/d | n/d | n/d |
| 19 | TFEOiBu | 16 | 66.25 | 0 | 0 | 0 | n/d |
| 20 | TFEOiBu/MeCN | 11 | 20.75 | 0.04 | n/d | n/d | n/d |
| 21 | MeOAcOMe | 53 | 2.0 | 0.29 | 0.40 | 0.42 | 3 |
| 22 | TFEHexanoate | 25 | 5.0 | 0.29 | 0.83 | 0.26 | 14 |
| 23 | TFELaurate | 15 | 5.0 | 0.54 | 0.88 | 0.38 | 26 |
| 24 | TFE2-MeButyrate | 25 | 5.0 | 0 | 0 | 0 | n/d |

Conditions: Runs 1, 4–9, 11–17, 19: (±)-IId, 4.9 mg; TBME or neat acylating agent, 1.0 mL; SP 435, 6.2–10.8 mg; 250 rpm; RT.
Runs 2, 21–24; (±)-IId, 9–12 mg; MeCN or neat acylating agent, 2.0 mL; SP 435, 5–7 mg; CaCO$_3$, 42–33 mg, 250 rpm, RT.
Runs 10, 18, 20: (±)-IId, 11–16 mg; Solvent, 2.0 mL; SP 435, 6–8 mg; NaHCO$_3$, 34–37 mg (except Run 10), 250 rpm, RT.
Run 3: (±)-IId, 15 mg; Acylating agent/solvent, 2.0 mL; SP435, 4 mg; 250 rpm, RT

E. Other Substrates

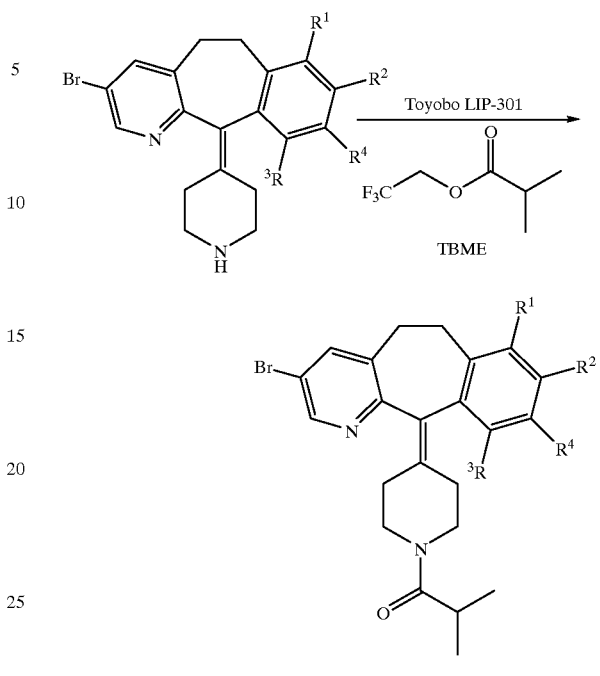

| Substrate | $R^1$ | $R^2$ | $R^4$ | $R^3$ | ee$_s$ or $[\alpha]_D^{25}$ | ee$_p$ or $[\alpha]_D^{25}$ | c | E |
|---|---|---|---|---|---|---|---|---|
| 1 | NH$_2$ | Cl | H | Br | 0.770 | 0.953 | 0.447 | 98 |
| 2 | H | Me | H | OMe | 0.520 | 0.989 | 0.345 | 311 |
| 3 | H | Cl | NH$_2$ | Br | −8.09° (c 1.484, MeOH) | +114.1° (c 0.142, MeOH) | n/d | n/d |

Conditions:
Run 1: 1, 5 mg; LIP-301, 10 mg; Trifluoroethyl isobutyrate, 10 equivs.; TBME, 1.0 mL; 200 rpm; RT
Run 2: 2, 5.4 mg; LIP-301, 16.6 mg; Trifluoroethyl isobutyrate, 20 equivs.; TBME, 1.0 mL; 200 rpm, RT.
Run 3: 3, 0.2 g; LIP-301, 0.4 g; Trifluoroethyl isobutyrate, 10 equivs.; TBME, 4 mL; 200 rpm, RT.

Following is a detailed example of a preferred embodiment of the process of this invention.

EXAMPLE 1

A mixture of (±)-IIc (20 g, 42.7 mmol, 98% pure by assay) in TBME (600 mL) was stirred at ambient temperature for 1 h, then filtered to remove a small amount of insoluble material. The solution was dried by azeotropic distillation; after 200 mL was distilled, a further 200 mL of TBME was added to the reaction mixture. After a total of 400 mL had been distilled, the moisture content (Karl-Fischer) of the solution was 214 ppm. Toyobo LIP-300 (40 g; 1282 ppm water) was added to the reaction mixture and stirred for 0.5 h; moisture content at this stage was 250 ppm. Trifluoroethyl isobutyrate (19.1 mL, 3 equivs.) was added and the mixture was stirred at ambient temperature. The reaction was terminated after 24 h. The enzyme was removed by filtration and washed with TBME (100 mL).

The combined filtrates were extracted with 0.5M H$_2$SO$_4$ (100 mL, 50 mL, 50 mL). The combined acidic extracts were added slowly (60 min) to a mixture of 50% NaOH (15 mL)

and water (150 mL). The solid which precipitated was filtered and dried to give (−)-Ic (10.6 g, 96% pure by assay, 52.1% yield; 76.7% ee).

The reaction mixture was extracted with 6M $H_2SO_4$ (2×30 mL). The combined extracts were heated to reflux for 8 h, cooled to room temperature, then added slowly (90 min.) to a mixture of 50% NaOH (70 mL) and ice (170 g), maintaining the temperature at <40° C. The precipitated solid was filtered and dried to give (+)-Ic (8.8 g, 97% pure by assay, 43.4% yield; 98.4% ee).

EXAMPLE 2

(−)II (27.30 g, 94% pure, 81.4% ee) was dissolved in diphenyl ether (137 mL) and heated at reflux under $N_2$ for 40 min., by which time the ee was <1%.

The mixture was cooled to room temperature and diluted with TBME (500 mL). Analysis of this solution showed a solution yield of 95.8%. The solution was extracted with 0.5 M $H_2SO_4$ (2×218 mL) and the combined acidic extracts were added slowly over a period of 1 hour to a vigorously stirred mixture of 50% NaOH (45 mL) and water (405 mL). After stirring for 0.5 hours, the precipitated solid was collected by filtration and washed with water (820 mL) (26.11 g, 94.6% yield, 1.0% ee).

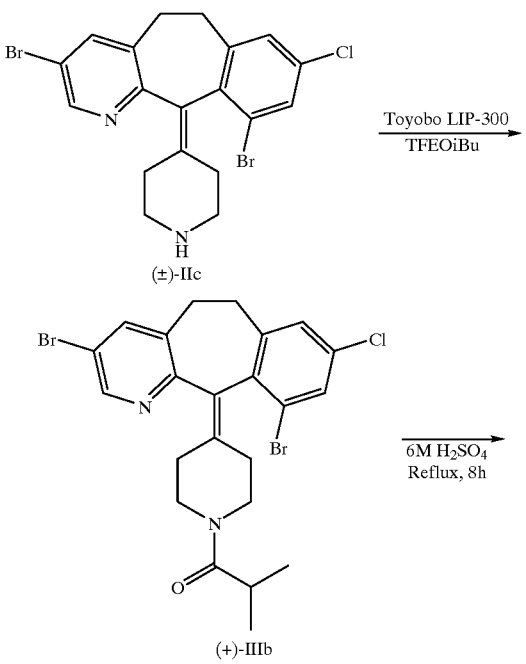

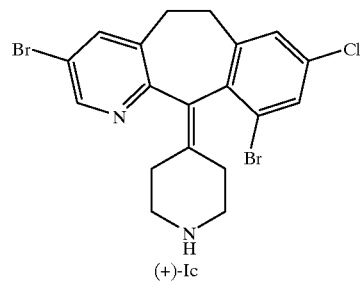

Enzymatic Resolution: 1st Cycle
Preparation of the R-isobutyramide (+)-IIIb (±)-IIc (93.0 g, 0.2 mol) was dissolved in TBME (2.0 L) and stirred at room temperature for 1 h. The reaction mixture was filtered, the insoluble material washed with more TBME (~1.0 L), and the volume of filtrate adjusted to 2.9 L. The solution of (±)-IIc was then dried by azeotropic distillation, removing 1.0 L of the solvent. The solution was cooled to room temperature and Toyobo LIP-301 (200 g) was added. After stirring at room temperature for 1 h, trifluoroethyl isobutyrate (90 mL, 0.56 mol) was added in one portion.

The reaction was stirred at room temperature under $N_2$ for 24 h. The enzyme was then removed by filtration and washed with TBME (0.9 L). The combined filtrates were extracted sequentially with three portions of 0.5 M $H_2SO_4$ (450 mL, 225 mL and 225 mL). These combined acidic extracts contained the unreacted (−)-IIc. The organic layer was then extracted with two portions of 6M $H_2SO_4$ (135 mL and 135 mL). These combined acidic extracts contained the product isobutyramide (+)-IIIb.

Isolation of (+)-Ic

The combined 6M $H_2SO_4$ extracts were heated at reflux for 14.5 h, then cooled to room temperature. The reaction mixture was then added slowly to a cold, vigorously stirred mixture of $NH_4OH$ (900 mL) and $CH_3CN$ (270 mL). The solid which precipitated was filtered, washed with water and dried (40.5 g, 43.5%; 0.960 ee).

Isolation of (−)-IIb

The combined 0.5 M $H_2SO_4$ extracts were added slowly to a cold, vigorously stirred mixture of $NH_4OH$ (450 mL) and $CH_3CN$ (270 mL). The solid which precipitated was filtered, washed with water and dried (40.5 g, 43.5%; 0.966 ee).

Racemization of (−)-IIb

Diphenyl ether (190 mL) was degassed under vacuum for 5–10 min and then purged with $N_2$ for 5–10 min. (−)-IIb (38 g, 81 mmol) was added and the mixture stirred under $N_2$ and heated to 245° C. The reaction mixture was maintained at 245° C. for 2 h, whereupon racemization was complete. After cooling to room temperature, the reaction mixture was diluted with TBME (570 mL) and filtered. The filtrate was extracted with two portions of 0.5 M $H_2SO_4$ (190 mL and 95 mL). The extracts were combined, charcoal (19 g) added, and the mixture heated to reflux for 1 h. After cooling, the mixture was filtered through Celite and the bed washed with 0.5 M $H_2SO_4$ (95 mL).

The combined filtrates were added slowly to a cold, vigorously stirred mixture of $NH_4OH$ (190 mL) and $CH_3CN$ (114 mL). The solid which precipitated was filtered, washed with water and dried (31.9 g, 84.0%).

A similar procedure can be carried out using diethylene glycol dibutyl ether in place of diphenyl ether, and heating at 210° C. for about 12 hours.

Enzymatic Resolution: 2nd Cycle

Racemized (±)-IIc (30 g, 64 mmol) was dissolved in TBME (600 mL), filtered and the volume adjusted to 900 mL. The solution was then dried by azeotropic distillation, removing 300 mL solvent. The mixture was cooled and Toyobo LIP-301 (60 g; recovered from 1st cycle above) was added. The mixture was stirred for 1 h, then trifluoroethyl isobutyrate (30 mL, 190 mmol) was added. After stirring at room temperature under $N_2$ for 24 h, the reaction mixture was then filtered and the enzyme cake washed with TBME (300 mL). The combined filtrate was extracted with three portions of 0.5 M $H_2SO_4$ (150 mL, 75 mL and 75 mL) to remove the unreacted (−)-IIc. The organic layer was then extracted with two portions of 6M $H_2SO_4$ (45 mL and 45 mL) which were combined and refluxed for 16h. The cooled reaction mixture was then added slowly to a vigorously stirred, cold mixture of $NH_4OH$ (300 mL) and $CH_3CN$ (90 mL). The precipitated (+)-IIc was filtered, washed with water and dried: (13 g, 43%; 0.986 ee).

We claim:

1. A process for preparing a substituted (6,11-dihydro-5H-benzo-[5,6]cyclohepta[1,2-b]pyridin-11-yl)piperidine compound of the formula (+)-I

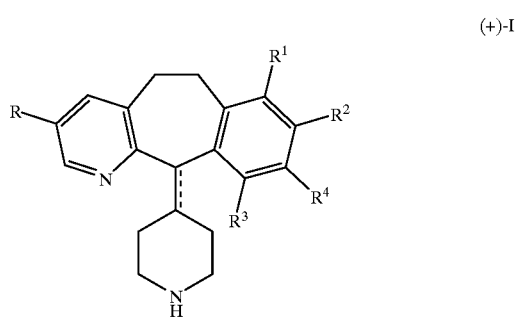

wherein:

R, $R^1$, $R^2$, $R^3$ and $R^4$ are independently selected from the group consisting of hydrogen, halo, $C_{1-C_6}$alkyl, amino, —$OCH_3$, —$OCF_3$ and $CF_3$, and the dotted line represents an optional double bond; comprising:

(1)
  (a) enzymatically catalyzing the acylation of a compound of formula (±)-II, wherein the variables are as defined above, to obtain a compound of formula (+)-III

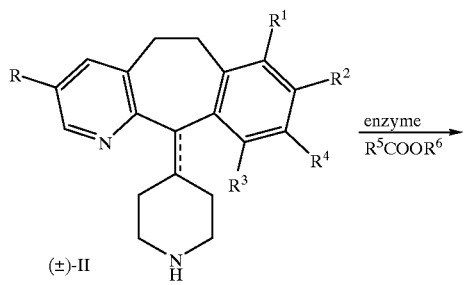

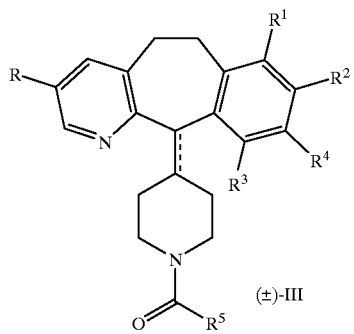

wherein the enzyme is a hydrolase and wherein the acylating agent is of the formula $R^5COOR^6$, wherein $R^5$ is $C_1-C_{15}$ alkyl, halo methyl, aryl, benzyl or benzyloxy, $R^6$ is $C_1-C_6$ alkyl, $C_1-C_6$ alkenyl, —$COR^7$, trifluoroethyl, —$CH_2CH(OCOR^7)CH_2OCOR^7$, halo methyl or benzyl, and $R^7$ is $C_1-C_{15}$ alkyl; and (b) hydrolysing the compound of formula (+)-III;
  (c) optionally converting an undesired isomer from step
    (a) wherein a double bond is present to the racemate by heating, and resubjecting the racemate to enzymatic acylation and hydrolysis; or (2) enzymatically catalyzing the acylation of a compound of formula (±)-IIa, wherein R, $R^1$, $R^2$, $R^3$ and $R^4$ are as defined above and the bond is a single bond, with a hydrolase, and wherein the acylating agent is as defined above.

2. The process of claim 1 wherein the enzyme is Toyobo LIP-300, Toyobo LIP-301, Altus Chiro CLEC™ PC or Novozym 435.

3. The process of claim 1 wherein the acylating agent is selected from the group consisting of trifluoroethyl acetate, trifluoroethyl butyrate, trifluoroethyl isobutyrate, trofluoroethyl benzoate, triacetin and tributyrin.

4. The process of claim 1 for preparing a compound of formula I wherein R, $R^2$ and $R^3$ are halo and $R^1$ and $R^4$ are hydrogen.

5. The process of claim 1 for preparing a compound of the formula

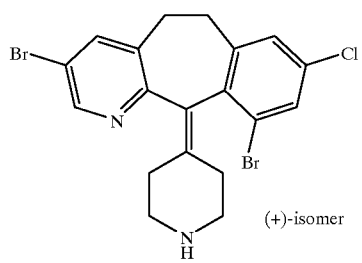

comprising enzymatically catalyzing the acylation a compound of the formula

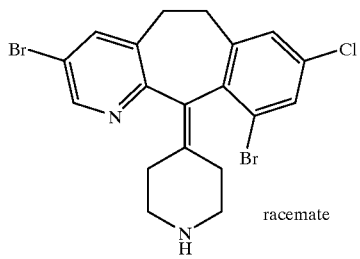

racemate using Toyobo LIP-300, Toyobo LIP-301 or Altus Chiro-CLEC™ PC as the enzyme and trifluoroethyl acetate, trifluoroethyl butyrate, trifluoroethyl isobutyrate, trifluoroethyl benzoate, triacetin or tributyrin as the acylating agent, followed by hydrolysis and optionally followed by reconversion of the undesired isomer to the racemate, and resubjecting the racemate to enzymatic acylation and hydrolysis.

6. The process of claim 1 wherein in step (c), the undesired isomer from step (a) is converted to the racemate by heating at 200–260° C. in diphenyl ether or diethylene glycol dibutyl ether.

7. The process of claim 5 wherein the undesired isomer is converted to the racemate by heating at 200–260° C. in diphenyl ether or diethylene glycol dibutyl ether.

8. The process of claim 1 for preparing a compound of the formula

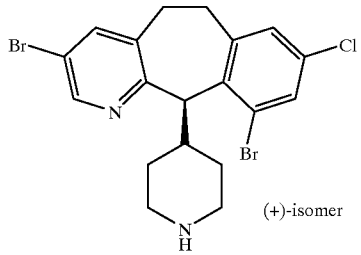

(+)-isomer comprising enzymatically catalyzing the acylation a compound of the formula

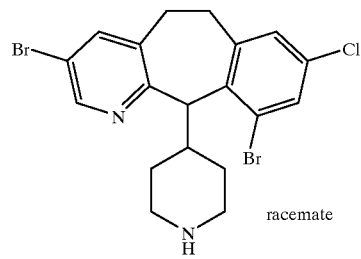

racemate using Toyobo LIP-300, Toyobo LIP-301 or Altus Chiro-CLEC™ PC as the enzyme and trifluoroethyl acetate or trifluoroethyl isobutyrate as the acylating agent, followed by hydrolysis.

9. The process of claim 1 for preparing a compound of the formula

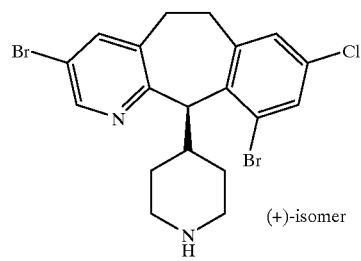

(+)-isomer comprising enzymatically catalyzing the acylation a compound of the formula

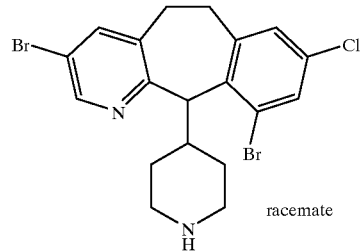

racemate using Novozyme SP435 as the enzyme and trifluoroethyl acetate, trifluoroethyl butyrate, trifluoroethyl hexanoate, trifluoroethyl laurate or methyl acetate as the acylating agent.

* * * * *